United States Patent [19]

Eldering et al.

[11] Patent Number: 5,622,930

[45] Date of Patent: Apr. 22, 1997

[54] C1 INHIBITOR MUTEINS AND USES THEREOF

[75] Inventors: Eric Eldering; Lucien Aarden, both of Amsterdam, Netherlands

[73] Assignee: CLB, Amsterdam, Netherlands

[21] Appl. No.: 755,573

[22] Filed: Sep. 5, 1991

Related U.S. Application Data

[63] Continuation-in-part of Ser. No. 617,920, Nov. 21, 1990, abandoned, which is a continuation of Ser. No. 428,202, Oct. 27, 1989, abandoned.

[51] Int. Cl.$^6$ .......................... A61K 38/57; C07K 14/81
[52] U.S. Cl. .......................... 514/12; 530/380; 530/395
[58] Field of Search ................................ 530/351, 380; 514/12, 21

[56] References Cited

U.S. PATENT DOCUMENTS

| | | | |
|---|---|---|---|
| 4,915,945 | 4/1990 | Pelzer et al. | 514/8 |
| 5,030,578 | 7/1991 | Pilatte et al. | 436/86 |
| 5,271,931 | 12/1993 | Lotz et al. | 424/85.1 |

OTHER PUBLICATIONS

Hack, et al. "*Elevated Plasma Levels of the Anaphylatoxins C3a and C4a are Associated with a Fatal Outcome in Sepsis,*" The American Journal of Medicine, 86:20–26 (Jan. 1989).

Schnebli, et al. "*Elgin c, a Pharmacologically Active Elastase Inhibitor,*" Eur. J. Respir Dis. 66, Suppl. 139, 66–70 (1985).

Bock et al. *Biochemistry* 25(15):4292–4301 (1986).

Eldering et al. *J. Biol. Chem.* 263(24):11776–79 (1988).

Skrive et al. *J. Biol. Chem.* 264(6)3066–71 (1989).

Schapira et al. *J. Clin. Invest* 80:582–585 (1987).

Eldering, E., et al., Sep. 10–15, 1989, Complement Inflammation, 6(5), Abstract No. 68, p. 333.

Eldering, E., et al. Sep. 10–15, 1989, Complement Inflammation, 6(5), Abstract No. 69, p. 333.

Primary Examiner—Stephen G. Walsh
Assistant Examiner—Karen E. Brown
Attorney, Agent, or Firm—Marshall, O'Toole, Gerstein, Murray & Borun

[57] ABSTRACT

Compositions consisting of C1 inhibitor muteins having biological activity similar to C1 inhibitor, but with enhanced resistance to proteolytic cleavage thus rendering such muteins suitable as anti inflammatory agents, preferably for the treatment or prevention of sepsis.

25 Claims, 6 Drawing Sheets

FIG. 1A

| | |
|---|---|
| CCAGAAGTTT GGAGTCCGCT GACGTCGCCG CCCAG ATG GCC TCC AGG CTG ACC<br>                    Met Ala Ser Arg Leu Thr<br>                    -22    -20 | 53 |
| CTG CTG ACC CTC CTG CTG CTG CTG GCT GGG GAT AGA GCC TCC TCA<br>Leu Leu Thr Leu Leu Leu Leu Leu Ala Gly Asp Arg Ala Ser Ser<br>  -15       -10          -5 | 101 |
| AAT CCA AAT GCT ACC AGC TCC AGC TCC CAG GAT CCA GAG AGT TTG CAA<br>Asn Pro Asn Ala Thr Ser Ser Ser Ser Gln Asp Pro Glu Ser Leu Gln<br>1      5         10        15 | 149 |
| GAC AGA GGC GAA GGG AAG GTC GCA ACA ACA GTT ATC TCC AAG ATG CTA<br>Asp Arg Gly Glu Gly Lys Val Ala Thr Thr Val Ile Ser Lys Met Leu<br>     20         25         30 | 197 |
| TTC GTT GAA CCC ATC CTG GAG GTT TCC AGC TTG CCG ACA ACC AAC TCA<br>Phe Val Glu Pro Ile Leu Glu Val Ser Ser Leu Pro Thr Thr Asn Ser<br>   35        40         45 | 245 |
| ACA ACC AAT TCA GCC ACC AAA ATA ACA GCT AAT ACC ACT GAT GAA CCC<br>Thr Thr Asn Ser Ala Thr Lys Ile Thr Ala Asn Thr Thr Asp Glu Pro<br>  50        55         60 | 293 |
| ACC ACA CAA CCC ACC ACA GAG CCC ACC ACC CAA CCC ACC ATC CAA CCC<br>Thr Thr Gln Pro Thr Thr Glu Pro Thr Thr Gln Pro Thr Ile Gln Pro<br>65       70         75        80 | 341 |
| ACC CAA CCA ACT ACC CAG CTC CCA ACA GAT TCT CCT ACC CAG CCC ACT<br>Thr Gln Pro Thr Thr Gln Leu Pro Thr Asp Ser Pro Thr Gln Pro Thr<br>       85         90        95 | 389 |
| ACT GGG TCC TTC TGC CCA GGA CCT GTT ACT CTC TGC TCT GAC TTG GAG<br>Thr Gly Ser Phe Cys Pro Gly Pro Val Thr Leu Cys Ser Asp Leu Glu<br>     100        105       110 | 437 |
| AGT CAT TCA ACA GAG GCC GTG TTG GGG GAT GCT TTG GTA GAT TTC TCC<br>Ser His Ser Thr Glu Ala Val Leu Gly Asp Ala Leu Val Asp Phe Ser<br>    115        120       125 | 485 |
| CTG AAG CTC TAC CAC GCC TTC TCA GCA ATG AAG AAG GTG GAG ACC AAC<br>Leu Lys Leu Tyr His Ala Phe Ser Ala Met Lys Lys Val Glu Thr Asn<br>  130        135        140 | 533 |
| ATG GCC TTT TCC CCA TTC AGC ATC GCC AGC CTC CTT ACC CAG GTC CTG<br>Met Ala Phe Ser Pro Phe Ser Ile Ala Ser Leu Leu Thr Gln Val Leu<br>145         150         155      160 | 581 |
| CTC GGG GCT GGG CAG AAC ACC AAA ACA AAC CTG GAG AGC ATC CTC TCT<br>Leu Gly Ala Gly Gln Asn Thr Lys Thr Asn Leu Glu Ser Ile Leu Ser<br>        165        170       175 | 629 |
| TAC CCC AAG GAC TTC ACC TGT GTC CAC CAG GCC CTG AAG GGC TTC ACG<br>Tyr Pro Lys Asp Phe Thr Cys Val His Gln Ala Leu Lys Gly Phe Thr<br>     180        185       190 | 677 |
| ACC AAA GGT GTC ACC TCA GTC TCT CAG ATC TTC CAC AGC CCA GAC CTG<br>Thr Lys Gly Val Thr Ser Val Ser Gln Ile Phe His Ser Pro Asp Leu<br>   195        200        205 | 725 |
| GCC ATA AGG GAC ACC TTT GTG AAT GCC TCT CGG ACC CTG TAC AGC AGC<br>Ala Ile Arg Asp Thr Phe Val Asn Ala Ser Arg Thr Leu Tyr Ser Ser<br>  210        215        220 | 773 |
| AGC CCC AGA GTC CTA AGC AAC AAC AGT GAC GCC AAC TTG GAG CTC ATC<br>Ser Pro Arg Val Leu Ser Asn Asn Ser Asp Ala Asn Leu Glu Leu Ile<br>225        230         235      240 | 821 |
| AAC ACC TGG GTG GCC AAG AAC ACC AAC AAC AAG ATC AGC CGG CTG CTA<br>Asn Thr Trp Val Ala Lys Asn Thr Asn Asn Lys Ile Ser Arg Leu Leu<br>        245        250       255 | 869 |

FIG. 1B

```
GAC AGT CTG CCC TCC GAT ACC CGC CTT GTC CTC CTC AAT GCT ATC TAC        917
Asp Ser Leu Pro Ser Asp Thr Arg Leu Val Leu Leu Asn Ala Ile Tyr
        260                 265                 270

CTG AGT GCC AAG TGG AAG ACA ACA TTT GAT CCC AAG AAA ACC AGA ATG        965
Leu Ser Ala Lys Trp Lys Thr Thr Phe Asp Pro Lys Lys Thr Arg Met
        275                 280                 285

GAA CCC TTT CAC TTC AAA AAC TCA GTT ATA AAA GTG CCC ATG ATG AAT       1013
Glu Pro Phe His Phe Lys Asn Ser Val Ile Lys Val Pro Met Met Asn
    290                 295                 300

AGC AAG AAG TAC CCT GTG GCC CAT TTC ATT GAC CAA ACT TTG AAA GCC       1061
Ser Lys Lys Tyr Pro Val Ala His Phe Ile Asp Gln Thr Leu Lys Ala
305                 310                 315                 320

AAG GTG GGG CAG CTG CAG CTC TCC CAC AAT CTG AGT TTG GTG ATC CTG       1109
Lys Val Gly Gln Leu Gln Leu Ser His Asn Leu Ser Leu Val Ile Leu
                325                 330                 335

GTA CCC CAG AAC CTG AAA CAT CGT CTT GAA GAC ATG GAA CAG GCT CTC       1157
Val Pro Gln Asn Leu Lys His Arg Leu Glu Asp Met Glu Gln Ala Leu
            340                 345                 350

AGC CCT TCT GTT TTC AAG GCC ATC ATG GAG AAA CTG GAG ATG TCC AAG       1205
Ser Pro Ser Val Phe Lys Ala Ile Met Glu Lys Leu Glu Met Ser Lys
            355                 360                 365

TTC CAG CCC ACT CTC CTA ACA CTA CCC CGC ATC AAA GTG ACG ACC AGC       1253
Phe Gln Pro Thr Leu Leu Thr Leu Pro Arg Ile Lys Val Thr Thr Ser
    370                 375                 380

CAG GAT ATG CTC TCA ATC ATG GAG AAA TTG GAA TTC TTC GAT TTT TCT       1301
Gln Asp Met Leu Ser Ile Met Glu Lys Leu Glu Phe Phe Asp Phe Ser
385                 390                 395                 400

TAT GAC CTT AAC CTG TGT GGG CTG ACA GAG GAC CCA GAT CTT CAG GTT       1349
Tyr Asp Leu Asn Leu Cys Gly Leu Thr Glu Asp Pro Asp Leu Gln Val
                405                 410                 415

TCT GCG ATG CAG CAC CAG ACA GTG CTG GAA CTG ACA GAG ACT GGG GTG       1397
Ser Ala Met Gln His Gln Thr Val Leu Glu Leu Thr Glu Thr Gly Val
            420                 425                 430

GAG GCG GCT GCA GCC TCC GCC ATC TCT GTG GCC CGC ACC CTG CTG GTC       1445
Glu Ala Ala Ala Ala Ser Ala Ile Ser Val Ala Arg Thr Leu Leu Val
            435                 440                 445

TTT GAA GTG CAG CAG CCC TTC CTC TTC GTG CTC TGG GAC CAG CAG CAC       1493
Phe Glu Val Gln Gln Pro Phe Leu Phe Val Leu Trp Asp Gln Gln His
    450                 455                 460

AAG TTC CCT GTC TTC ATG GGG CGA GTA TAT GAC CCC AGG GCC              1535
Lys Phe Pro Val Phe Met Gly Arg Val Tyr Asp Pro Arg Ala
465                 470                 475

TGAGACCTGC AGGATCAGGT TAGGGCGAGC GCTACCTCTC CAGCCTCAGC TCTCAGTTGC     1595

AGCCCTGCTG CTGCCTGCCT GGACTTGCCC CTGCCACCTC CTGCCTCAGG TGTCCGCTAT     1655

CCACCAAAAG GGCTCCTGAG GGTCTGGGCA AGGGACCTGC TTCTATTAGC CCTTCTCCAT     1715

GGCCCTGCCA TGCTCTCCAA ACCACTTTTT GCAGCTTTCT CTAGTTCAAG TTCACCAGAC     1775

TCTATAAATA AAACCTGACA GACCATAAAA AAAAA                                1810
```

CIS  FIG. 3A
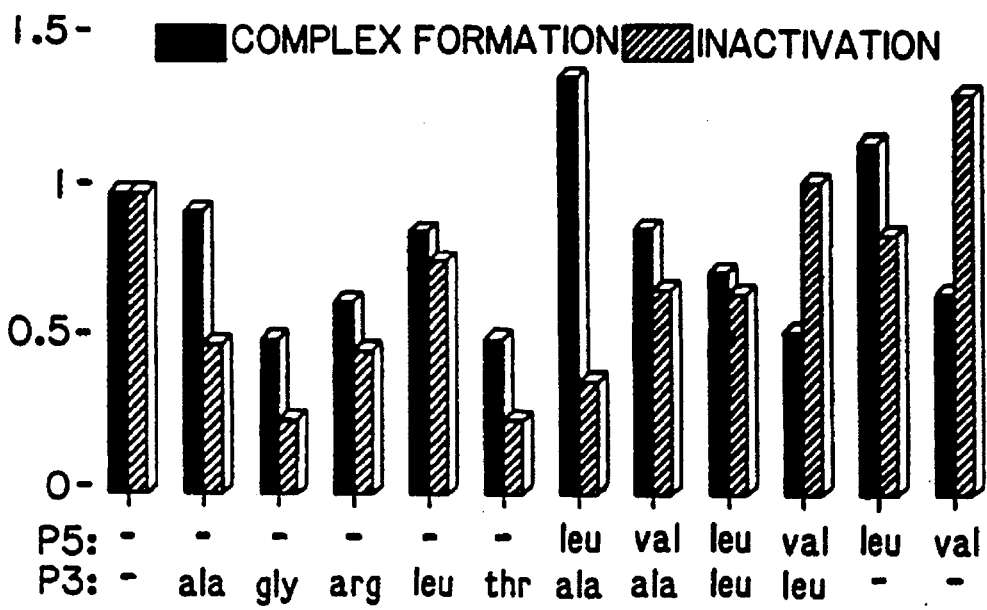
KALLIKREIN  FIG. 3B
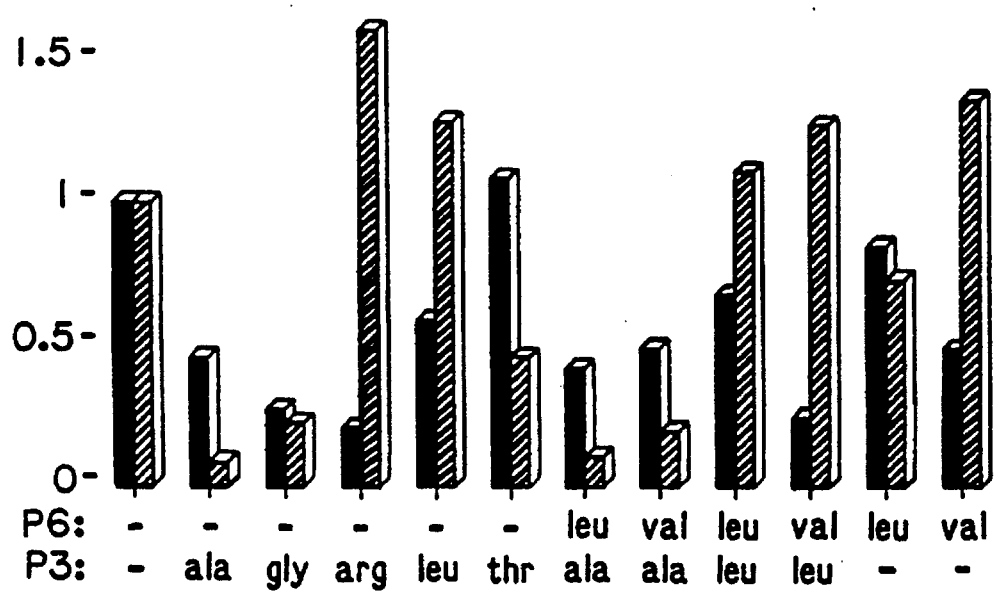

A DASH (—) MEANS WILD TYPE RESIDUE.

C1 INHIBITOR MUTEINS AND USES THEREOF

This application is a continuation-in-part of U.S. Ser. No. 617,920, filed Nov. 21, 1990, now abandoned, which in turn is a continuation application of U.S. Ser. No. 428,202, filed Oct. 27, 1989, now abandoned.

FIELD OF THE INVENTION

This invention is in the area of molecular biology/immunology, and presents genetically engineered constructs of C1 inhibitor, termed C1 inhibitor muteins, that are resistant to proteolytic attack. The muteins have considerable applications, preferably as anti-inflammatory agents and more preferably for the prophylactic or therapeutic treatment of sepsis.

BACKGROUND OF THE INVENTION

In the United States alone nosocomial bacteremia develops in about 194,000 patients, and of these about 75,000 die. Maki, D. G., 1981, *Nosocomial Infect.*, (Dikson, R. E., Ed.), page 183, Yrke Medical Books, U.S.A. Most of these deaths are attributable to six major gram-negative bacilli, and these are *Pseudomonas aeruginosa, Escherichia coli*, Proteus, Klebsiella, Enterobacter and Serratia. The current treatment for bacteremia is the administration of antibiotics which, unfortunately, have limited effectiveness.

The precise pathology of bacteremia is not completely elucidated, nevertheless, it is known that bacterial endotoxins, lipopolysaccharides (LPS), are the primary causative agent. LPS consist of at least three significant antigenic regions, the lipid A, core polysaccharide, and O-specific polysaccharide. The latter is also referred to as O-specific chain or simply O-antigen. The O-specific chain region is a long-chain polysaccharide built up from repeating polysaccharide units. The number of polysaccharide units differs among different bacterial species and may vary from one to as many as six or seven monosaccharide units. While the O-specific chain varies among different gram-negative bacteria, the lipid A and core polysaccharides are similar if not identical.

Since LPS plays a key role in sepsis, a variety of approaches has been pursued to neutralize its activity. Presently, there is considerable work which suggest that antibody to LPS will soon be a valuable clinical adjunct to the standard antibiotic therapy.

LPS initiates a cascade of biochemical events that eventually causes the death of the patient. It is widely believed that the second event, after the introduction of LPS, is the production of tumor necrosis factor (TNF) as a result of LPS stimulation of macrophage cells. Thus, considerable effort has been expended to produce neutralizing antibody to TNF, or other molecules that could inhibit its septic effects. It is likely that antibody to TNF will have valuable clinical applications. Tracey, et all., 1987, *Nature*, 330: 662.

Sepsis caused by gram-negative bacteria is thought to involve activation of the complement system and causes a depletion of various complement component. One component of a complement system, C5a, causes the aggregation of neutrophils and the aggregates are thought to embolize and cause ischemia. Siegel, J., 1981, *Ann. Rev. Med.*, 32: 175. It has been proposed that C5a is thus responsible for the observed organ failure phenomena in sepsis.

C1 is a plasma glycoprotein with a molecular weight of about 105,000 and is a member of the super family of serine protease inhibitors which include such members as α1-antitrypsin, α1-antiplasmin, antithrombin III, and plasminogen activator inhibitor types I and II. One mechanism by which the activator components of the complement system are controlled is by the C1 inhibitor. The C1 inhibitor is known to inhibit activating components of the classical pathway of complement (C1r and C1s) and the intrinsic coagulation system (Factor XIa, Factor XIIa, and Kallikrein). Further, C1 inhibitor has been shown to interact with the fibrinolytic components plasmin and tissue plasminogen activator.

C1 inhibitor is susceptible to proteolytic cleavage by so called non-target proteases, particularly lysosomal serine protease elastase. Browere, M. and Harpel, P., 1982, *J. Biol. Chem.*, 257: 9849. This enzyme is released from polymorphonuclear leukocytes and is present in the circulation of septaremic patients. It is thought that the decrease in the concentration of coagulation factors observed in these patients may, in part, be the result of proteolysis by leukocyte elastase of C1 inhibitor. It will be appreciated, that a possible prophylactic/therapeutic approach to treating sepsis would be to genetically engineer C1 inhibitors that are resistant to proteolytic cleavage and administer these to patients that are at risk of contracting sepsis, or that are already septic.

The life threatening nature of sepsis mandates the identification and development of additional therapeutics or prophylactics, both antibody based or otherwise, that may be efficaciously applied in the treatment of sepsis.

SUMMARY OF THE INVENTION

In its most general form, the invention described herein presents C1 inhibitor muteins, methods of constructing the muteins, and applications of the muteins, preferably as anti-inflammatory agents and more preferably for the prophylactic or therapeutic treatment of sepsis.

A second object of the invention described herein relates to C1 inhibitor muteins that are both elastase resistant, and that maintain the capacity to covalently bind to, and inactivate components of the complement system.

A third object of the invention is a description of C1 inhibitor muteins that have amino acids at positions 440 and/or 442 mutated to another suitable amino acid, or deleted, that are both elastase resistant, and that maintain the capacity to covalently bind to, and inactivate components of the complement system.

A fourth object of the invention is a description of C1 inhibitor muteins that display differential sensitivity to proteases and inhibitory activity depending on the type of amino acid that is substituted for amino acids at positions 440 and/or 442.

A fifth object of the invention is a description of C1 inhibitor muteins that exhibit differential inhibitory activity towards various substrates depending on the type of amino acid that is substituted for amino acids at positions 440 and/or 442.

Further, the invention concerns the prophylactic or therapeutic use of C1 inhibitor muteins as anti-inflammatory medicaments, and preferably for the prophylactic or therapeutic treatment of sepsis.

These and further objects of the invention will become apparent after a consideration of the detailed description of the invention shown below.

BRIEF DESCRIPTION OF THE DRAWINGS

FIGS. 1A and 1B (FIG. 1A and FIG. 1B), when combined in consecutive order, disclose both a cDNA sequence that encodes a C1 inhibitor and the corresponding C1 inhibitor encoded thereby. In FIG. 1B, the solid triangle pointing between amino acid residues 444 (the P1 residue) and 445 (the P1' residue) indicates the protease C1 esterase cleavage site.

FIGS. 3A and 3B compare inhibitory activity (complex formation) as the solid bars and protease sensitivity (inactivation) as the striped bars, by C1 inhibitor muteins having the indicated amino acid substitutions in the wild-type C1 inhibitor of FIG. 1 at residue position 442 (the "P3" residue) and/or residue position 440 (the "P5" residue), relative to the wild-type C1 inhibitor of the first column as measured against the proteases C1$s$ (FIG. 3A) and kallikrein (FIG. 3B).

DETAILED DESCRIPTION OF THE INVENTION

1. Definitions

Figure 2:
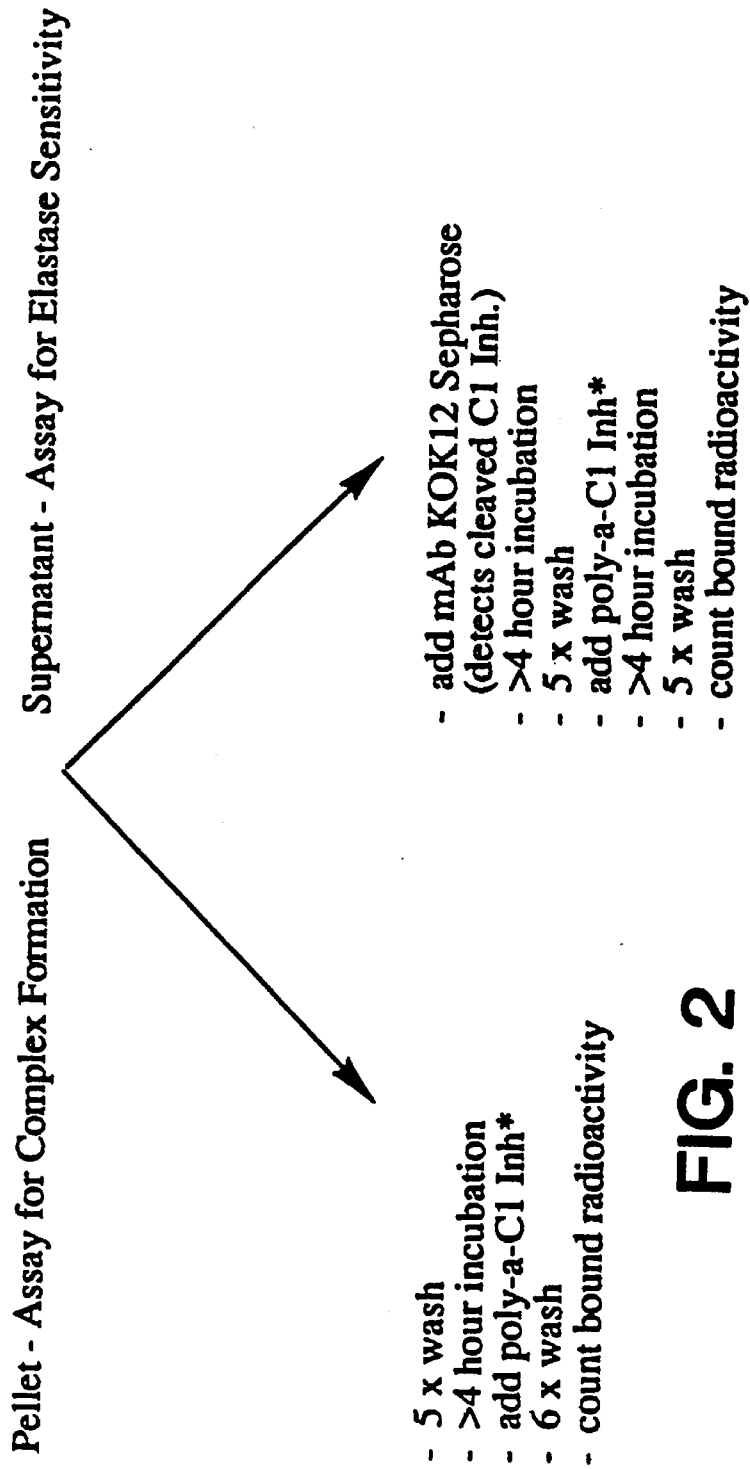
FIG. 2. schematically presents a generalized assay procedure for determining the inhibitory or protease sensitivity of the C1 muteins.
Figure 4A:
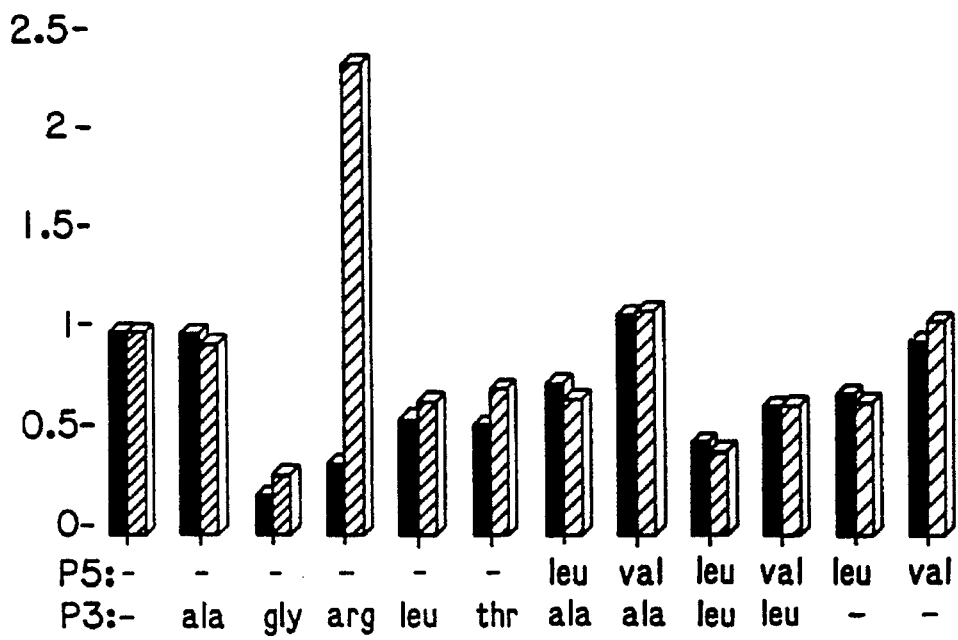
FIGS. 4A and 4B compare inhibitory activity (complex formation) as the solid bars and protease sensitivity (inactivation) as the striped bars, by C1 inhibitor muteins having the amino acid sequence of the wild-type C1 inhibitor of FIG. 1 as modified by the indicated amino acid substitutions, relative to the wild-type C1 inhibitor of the first column, as measured against B-12$a$ and plasmin.
Figure 4B:
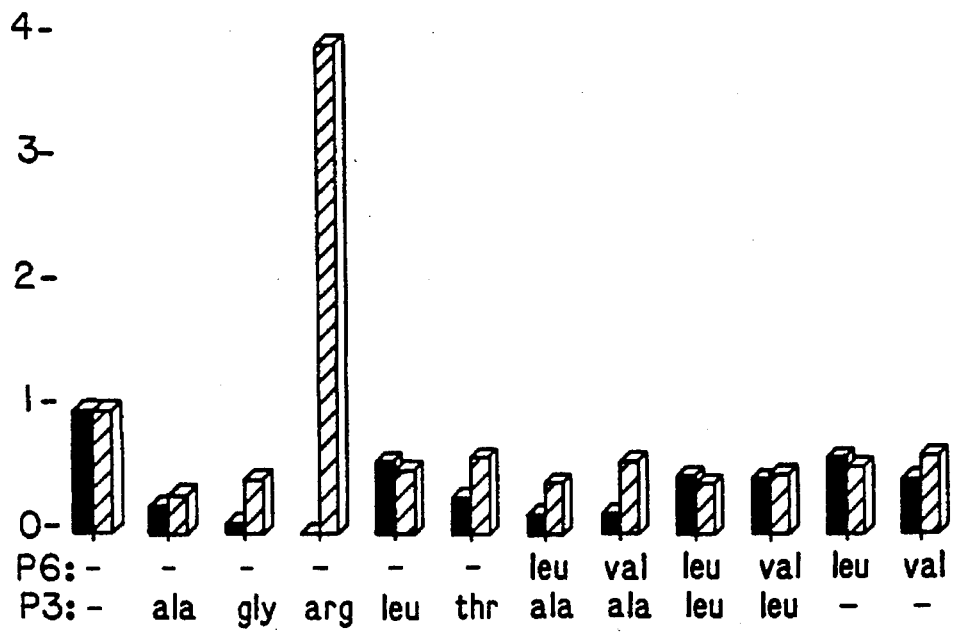
Figure 5:
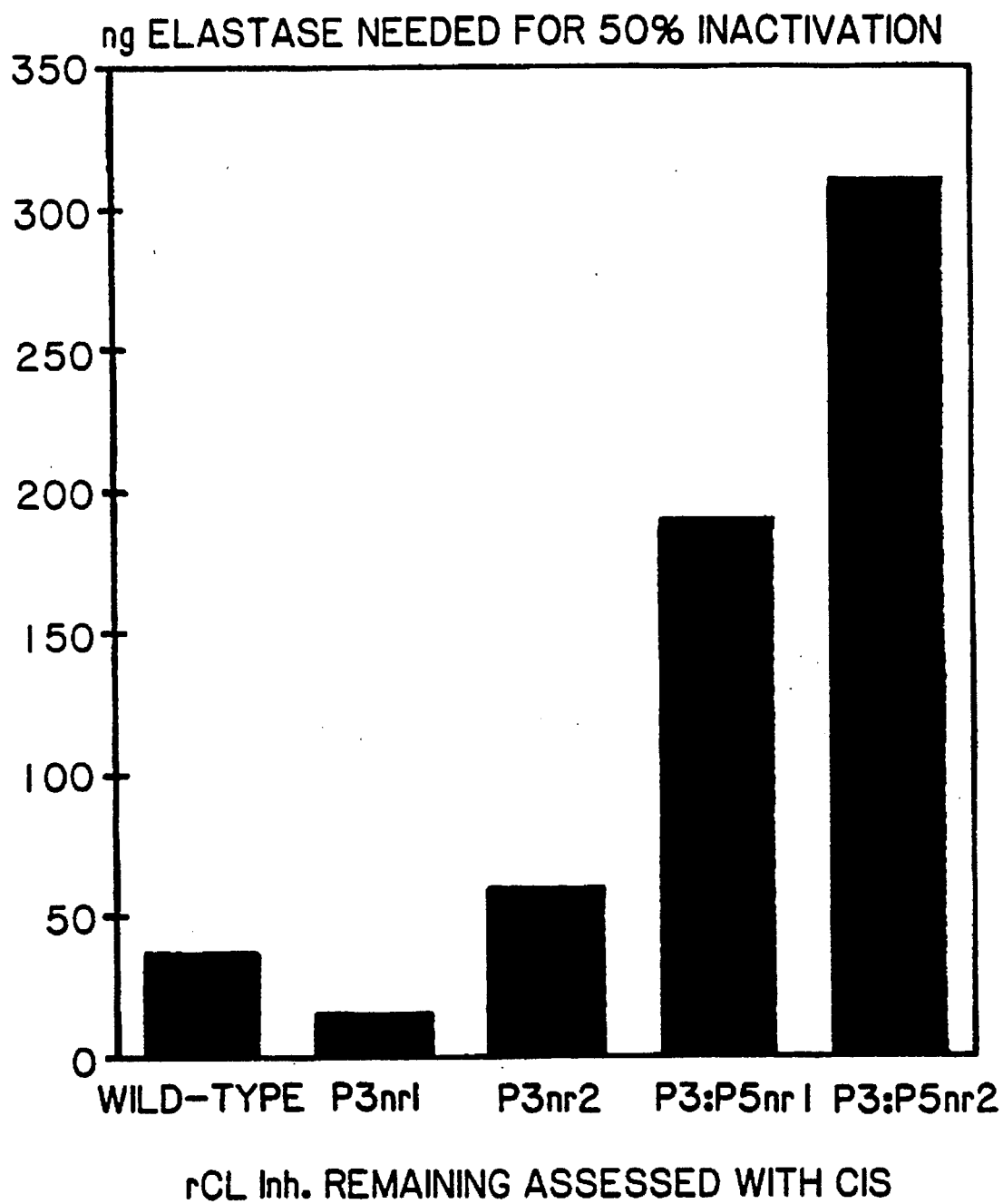
FIG. 5 shows the amount of neutrophil elastase needed for 50% inhibition of several C1$s$ inhibitor muteins.

To facilitate understanding the nature and scope of applicant's invention, several definitions regarding various aspects of the invention are presented below. It will be understood, however, that these definitions are general in nature, and encompassed within the definitions are meanings well known to those skilled in the art.

Sepsis is herein defined to mean a disease resulting from gram-positive or gram-negative bacterial infection, the latter primarily due to the bacterial endotoxin, lipopolysaccharide (LPS). It can be induced by at least the six major gram-negative bacilli and these are *Pseudomonas aeruginosa, Escherichia coli,* Proteus, Klebsiella, Enterobacter and Serratia.

By C1 inhibitor is meant a plasma glycoprotein with a molecular weight of about 105,000 that belongs to the super family of serine protease inhibitors. It inhibits activated components of the classical pathway of complement, C1$r$ and C1$s$, and the intrinsic coagulation system, factor XIa, factor XIIa, and Kallikrein. C1 also interacts with plasmin and tissue plasminogen activator. C1 has the further property of itself being inactivated by proteases, notably elastase. It will, or course, be understood that intended to come within the scope of the definition of the C1 inhibitor are fragments of the molecule that maintain biologically activity.

By C1 inhibitor mutein is meant a molecule that has the biological activity of C1 inhibitor, although to different degrees as exemplified by the data of the invention, and is particularly resistant to proteolytic attack.

Several patents/patent applications and scientific references are referred to below. The instant invention draws on some of the material and methods shown in these references, and thus it is intended that all of the references, in their entirety, be incorporated by reference.

2. C1 Inhibitor Muteins

C1 inhibitor has been cloned and expressed and thus is readily available to the practitioner to perform the herein described mutagenesis. For example, cloning of C1 inhibitor is described by Bock, et al., 1986, *Biochemistrye,* 25: 4292. The cDNA sequence is shown in FIG. 1. Further, Eldering, et al., 1988, *J. Biol. Chem.,* 263: 11776, show a Aat II-HaeII C1 inhibitor cDNA fragment that encodes the entire molecule. This fragment can be manipulated using the procedures described below to generate the C1 inhibitor muteins.

Mutein Construction—General Procedures

Construction of suitable vectors containing the desired coding and control sequences for the Aat II-HaeII C1 inhibitor cDNA fragment employs standard ligation and restriction techniques which are understood in the art. Isolated plasmids, DNA sequences, or synthesized oligonucleotides are cleaved, tailored, and religated in the form desired.

More specifically, site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20λ of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol and resuspension in 10 mM Tris, 1 mM EDTA, pH 7.5. If desired, size separation of the cleaved fragments may be performed by polyacrylamide gel or agarose gel electrophoresis using standard techniques. A general description of size separations is found in *Methods in Enzymology,* 1980, 65: 499–560.

Restriction cleaved fragments may be blunt ended by treating with the large fragment of *E. Coli* DNA polymerase I (Klenow) in the presence of the four deoxynucleotide triphosphates (dNTPs) using incubation times of about 15 to 25 minutes at 20° to 25° C. in 50 mM Tris pH 7.6, 50 mM NaCl, 6 mM $MgCl_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci et al., 1981, *J. Am, Chem. Soc.,* 103: 3185, or using commercially available automated oligonucleotide synthesizers. Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl2, 5 mM dithiothreitol, 1–2 mM ATP, 1.7 pmoles γ32P-ATP (2.9 mCi/mmole), 0.1 mM spermidine, 0.1 mM EDTA.

Ligations are performed in 15–30 λ volumes under the following standard conditions and temperatures: 20 mM Tris-Cl pH 7.5, 10 mM MgCl$_2$, 10 mM DTT, 33 µg/ml BSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per µg of vector at 60° C. for about 1 hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a synthetic primer oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

Correct ligations for plasmid construction are confirmed by first transforming *E. coli* strain MM294 obtained from *E. coli* Genetic Stock Center, CGSC#6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., 1969, *Proc. Nat. Acad. Sci. (USA)*, 62: 1159, optionally following chloramphenicol amplification (Clewell, D. B., 1972, *J.Bacteriol.*, 110: 667). The isolated DNA is analyzed by restriction and/or sequenced by the dideoxy method of Sanger, F., et al., 1977, *Proc. Natl. Acad. Sci.(USA)*, 74: 5463 as further described by Messing et al, 1981, *Nucleic Acids Res.*, 9: 309, or by the method of Maxam et al., 1980, *Methods in Enzymology*, 65: 499.

Depending on the host cell used, transformation is done using standard techniques appropriate to such cells. The calcium treatment employing calcium chloride, as described by Cohen, S. N.,*Proc. Nat. Acad. Sci. (USA)* (1972) 69: 2110, or the RbCl$_2$ method described in Maniatis et al., *Molecular Cloning: A Laboratory Manual* (1982) Cold Spring Harbor Press, p. 254 was used for procaryotes or other cells which contain substantial cell wall barriers. For mammalian cells without such cell walls, the calcium phosphate precipitation method of Graham and Van der Eb, *Virology*, 1978, 52: 546 is preferred.

Host strains used in cloning and expression herein are as follows. For cloning and sequencing, *E.coli* strain HB101 may be used as the host. For M13 phage recombinants, *E. coli* strains susceptible to phage infection, such as *E.coli* K12 strain DG98 are employed. The DG98 strain has been deposited with the American Type Culture Collection, 12301 Parklawn Drive, Rockvile, Md. 20852 on 13 July 1984 and has accession number 1965. A preferred expression system for the C1 inhibitor muteins is the COS-1cell/pSVL vector system shown by Eldering et al., 1988, *Journal of Biological Chemistry*, 263: 11776. pSVL (Pharmacia, Uppsala, Sweden) consists of the SV40 origin of replication, the SV40 late promoter, and the VP1 intron in front of a polylinker followed by the SV40 late polyadenylation signal, fused to a pBR322 fragment containing the origin of replication and ampicillin resistance gene.

Mutagenesis can be carded out using any number of procedures known in the art. These techniques are described by Smith, 1985, *Annual Review of Genetics*, 19: 423, and modifications of some of the techniques are described in *Methods in Enzymology*, 154, part E, (eds.) Wu and Grossman (1987), chapters 17, 18, 19, and 20. The preferred procedure is a modification of the Gapped Duplex site-directed mutagenesis method which is described by Kramer, et al., in chapter 17 of volume 154 of *Methods in Enzymology*, above; and by Kramer et al., 1984, *Nucleic Acids Research*, 12: 9441.

Mutein Construction—Preferred Procedures

Conventional M13 mutagenesis methods involve annealing a short synthetic oligonucleotide to single stranded M13 DNA having a cloned target coding sequence that is sought to be mutagenized. The oligonucleotide is almost, but not entirely complementary to the target sequence and has at least one mispaired nucleotide. After the annealing reaction, the remaining portion of the single stranded DNA must be filled in to give heteroduplex DNA that can be transfected into a suitable host cell which allows for the expression of the mutation. In the gapped duplex method, as described by Kramer, et al., in chapter 17 of the *Methods in Enzymology*, a partial DNA duplex is constructed that has only the target region exposed, unlike the conventional methods which have the target region and the rest of the single stranded M13 DNA exposed. Like the conventional methods, a short oligonucleotide is annealed to the target region, and extended and ligated to produce a heteroduplex. However, because only a small portion of single-stranded DNA is available for hybridization in the gapped duplex method, the oligonucleotide does not anneal to undesired sites within the M13 genome. This method has the additional advantage of introducing fewer errors during the formation of the heteroduplex since only a very small region of DNA on either side of the target region has to be filled in.

More specifically, the gapped duplex method involves cloning the target Aat II-HaeII C1 inhibitor cDNA fragment into an appropriate M13 phage that carries selectable markers, such as, for example, the stop codon amber mutation. The latter allows for negative selection in a host cell that cannot suppress the effects of the mutation. Preferably the phage is M13mp9 which contains two amber codons in critical phage genes. Thus, the sequence that encodes C1 is cloned into M13mp9 amber+, and single stranded DNA is prepared therefrom using standard techniques. Next, double stranded replicative form DNA from M13 GAP, a genetically engineered M13 derivative that lacks the amber codons is cleaved with the appropriate restriction enzyme. The base sequence of M13 GAP is similar to M13mp18, which lacks both the amber codons and the sequence between base pairs 6172 and 6323. This deletion flanks the multiple cloning sites of the M13mp series and generates a unique restriction site. Gapped duplex DNA is formed, using standard DNA/DNA hybridization techniques, consisting of single stranded DNA having the amber codons, and a second strand of DNA from digested M13 GAP lacking both the amber codons and the C1 coding sequences. Thus, the only portion of the gapped duplex that is exposed is the C1 target sequence. The desired oligonucleotide(s) is annealed to the gapped duplex DNA, and any remaining gaps filled in with DNA polymerase and the nicks sealed with DNA ligase to produce a heteroduplex. As applied to the instant invention mutagenesis was performed with a mixture of oligonucleotides that code for 16 different muteins. The sequence of the degenerate oligonucleotide used is:

(SEQ ID NO: 1)

The oligonucleotide is complementary to nucleotides 1412–1433 of Bock et al., above.

In addition to the above, several other single P3 muteins were obtained using the following oligonucleotides:

P3-ala (SEQ ID NO: 2)

P3-gly (SEQ ID NO: 3)

P3-arg (SEQ ID NO: 4)

P3-leu (SEQ ID NO: 5)

P3-thr (SEQ ID NO: 6)

The heteroduplex is transfected, preferably into a mismatch repair deficient host, and mixed phage produced. From the mixed phage population, phage carrying unmutated C1 DNA, which also have the amber mutations, can be selected against by infecting the mixed phage population into a host cell that cannot suppress the amber mutation. Clones can then be screened for phage that carry a C1 mutation, and the molecules sequenced to determine the position of the mutation. Clones were screened using a mixture of kinased degenerate oligonucleotides. Using the foregoing method, 11 C1 inhibitor muteins were produced.

C1 inhibitor mutein DNA fragments were excised from M13 with the appropriate restriction enzymes and cloned into a vector suitable for expression in COS cells. The vector is pSVL and is shown in Bock et al., above. Alternatively pC1-INH, also described by Bock et al., could be used.

SV4O-transformed COS-1 monkey cells were grown in Iscove's Modified Dulbecco Cell Culture Medium containing penicillin and streptomycin. The media was supplemented with 10% v/v) heat-inactivated fetal calf serum. Transfection of the cells was performed essentially as described by Luthmann, and Magnusson, 1983, *Nucleic Acids Research,* 5: 1295. This consisted of incubating subconfluent COS-1 cells in the cell culture media for 90 minutes with supercoiled vector encoding C1 inhibitor mutein DNA (5–7.5 μg/ml) and DEAE-dextran (200 μg/ml). After a 90 minute incubation period, the cells were washed twice with cell culture media, and incubated for an additional 2 hours with cell culture media containing 80 μg/ml chloroquine. Two further washes were performed, and the cells incubated with cell culture media supplemented with 10% fetal calf serum. This media was replaced 24 hours later with serum free media. The latter media was harvested after 72 hours, centrifuged to remove cells and debris, and assayed for C1 inhibitor activity, as described below.

Assay for C1 inhibitor Mutein Activities

FIG. 2 presents a generalized assay screening format for determining both the inhibitory (complex formation) or protease sensitivity (inactivation) of the C1 muteins. The latter measures inactivation of the C1 inhibitor muteins by non-target proteases. This procedure is also described by Eldering et al., 1988, in *J. of Biological Chem.,* 263: 11776. Modifications of these methods are also known in the art.

Generally, inhibitor activity of C1 muteins may be determined by measuring complex formation between the C1 inhibitor and a substrate. The preferred substrates are, of course, C1*s*, Kallikrein, B-12*a*, and plasmin. The C1 inhibitor, or C1 inhibitor muteins, inhibit the protease activity of the substrate by forming a covalent bond with the substrate. These molecules were purified by techniques known in the art, or as described by Liebermann, H., etal., 1984, *J. Mol. Biol.,* 177: 531 and Nuijens, J.,et al., 1987, *Immunology,* 61: 387.

Many procedures are available for measuring the complex resulting from the interaction of the C1 inhibitor mutein and its target proteinase substrate, and include standard immunochemical, radiochemical, or elisa assays. Levin, M., et al., 1983, *J. Biol. Chem.,* 258: 6415, Nuijens, J., et al., 1987, *Thromb, Haemost.,* 58: 778, de Agostini, 1985, *pNAS,* 82: 5190. The procedures generally consist of contacting a C1 inhibitor mutein with a target substrate in solution to permit complex formation to occur, then separating the complex from uncomplexed reactants, and detecting the amount of complex formed. Other assays may be employed whereby the amount of reactants, that is, free C1 inhibitor mutein or target molecule, remaining in the reaction solution are measured after complex formation has occurred.

The preferred assay is a radioimmune assay based on the observation that functional C1 inhibitor muteins bind to activated target substrate, such as C1*s*. The assay can be performed in several ways, but preferably purified activated C1*s* is coupled to a solid matrix, preferably Sepharose 4B via cyanogen bromide as is known in the art. Coupled C1*s* is incubated in an appropriately buffered solution containing, if desired, a small amount of detergent, preferably Tween-20. The latter is used at a concentration of about 0.1% (w/v). The capacity of the C1 inhibitor muteins to complex with the target substrate can be detected using anti-C1 inhibitor mutein antibody. Alternatively, a radiolabelled second antibody can be used to detect the bound first antibody. The antibody may be polyclonal or monoclonal and is incubated for a sufficient time to permit detectible binding of the antibody to the C1 inhibitor to occur. After the appropriate washing steps are conducted whereby nonspecifically bound radiolabelled antibody is separated from antibody bound to C1 inhibitor muteins, the amount of radioactivity associated with the latter is determined. In this way, and incorporating the appropriate controls in the assay scheme, the inhibitory capacity of the C1 muteins is determined.

Using similar approaches, the non-target protease sensitivity of the C1 inhibitor muteins may be determined. Numerous assays may be employed that measure the amount of intact C1 inhibitor mutein, or fragments that are derived from the muteins, remaining after exposure to protease. Many procedures are available for measuring the protease sensitivity of the C1 inhibitor muteins, and include standard immunochemical, radiochemical, or elisa assays. A solid phase assay is preferred whereby C1 inhibitor muteins are reacted with non-target protease bound to a solid matrix and the amount of proteolysis of the muteins measured by determining the amount of intact mutein remaining, or preferably by detecting fragments of the mutein. Alternatively, the C1 inhibitor mutein may be bound to a solid support matrix and this material subjected to proteolysis provided attachment of the mutein does not stericly interfere with protease accessability to the mutein.

An exemplary non-target protease that cleaves C1 is neutrophil elastase. Thus, this enzyme may be coupled to CNBr treated Sepharose 4B, and incubated with a C1 inhibitor mutein, and the presence of proteolytically cleaved C1 mutein monitored using a number of techniques. The preferred procedure is to pellet the Sepharose-coupled elastase, and measure the presence of cleaved C1 inhibitor in the supernatant using an antibody that recognizes this molecule. Such antibodies are available and are described by Nuijens, et al., 1988, *Blood,* 22: 1841. They may be attached to a solid matrix to facilitate separating the cleaved C1 inhibitor mutein from the other reactants. The Sepharose beads containing antibody having bound cleaved C1 mutein inhibitor are spun down, washed and separated from the supernatant containing uncleaved C1 inhibitor or cleaved but unbound fragments. Subsequently, the amount of bound cleaved C1 inhibitor can be determined using a second radiolabelled antibody that recognizes the cleaved molecule. Finally, the amount of radioactivity adherent to the Sepharose beads may be determined as an indication of the amount of cleavage resulting from elastase.

The general procedures for determining both the inhibitory or non-target protease sensitivity of the C1 inhibitor muteins are shown in FIG. 2. The procedures involving C1*s* will be described briefly, the procedures for the other substrates is similar with modifications as noted by Eldering, 1988, *J. Biological Chem.*, 263: 11776, and as shown by Nuijens et al., above.

As mentioned above, the radioimmune assay to determine the C1 inhibitor activity of the various muteins is based on the observation that functional C1 inhibitor mutein will bind to activated C1*s*. Thus, purified activated C1*s* is coupled to CNBr Sepharose 4B and suspended in phosphate-buffered saline, pH 7.4 10 mM EDTA, and 0.1% (w/v) Tween-20. Next, 0.3 ml of this mixture containing 1.5 μg of activated C1*s* is incubated with various dilutions of the C1 inhibitor muteins for 5 hours. The Sepharose 4B beads are collected, extensively washed, and complexed C1 inhibitor mutein incubated (>4hours) with $^{125}$I-polyclonal anti-C1 antibody. The antibody is described by Hack, et al., above. The Sepharose beads are washed, and bound radioactivity determined using a LKB 1260 multigamma II gamma counter.

Inactivation of the C1 inhibitor muteins is determined as follows. Porcine pancreatic elastase is coupled to Sepharose 4B such that about 3.75 mg of elastase is coupled to 300 mg of Sepharose. The beads are suspended in phosphate buffered saline containing 10 mM EDTA, and 0.1% w/v Tween-20. Various amounts of C1 inhibitor muteins are incubated with 150 μl of Sepharose 4B suspension containing 5.6 mg of elastase in 500 μl of volume for 1 hour at room temperature. Subsequently, the mixture is centrifuged, and the supernatant assayed for the presence of inactivated C1 inhibitor mutein using KOK12 monoclonal antibody bound to Sepharose, and polyclonal $^{125}$I-anti-C1-inhibitor antibodies, as described above.

FIG. 3 shows the degree of inhibitory activity (complex formation) and protease sensitivity (inactivation) of 11 C1 inhibitor muteins as assessed using C1*s* and Kallikrein as substrates and neutrophil elastase as the source of protease. FIG. 4 shows the same data with the exception that the substrates were B-12*a* and plasmin.

It is noteworthy that the 11 C1 inhibitor muteins exhibit considerable variation in inhibitor activity, and protease sensitive. This was a function of both the type of amino acid used to substitute for the wild type amino acid, and the substrates used to test for inhibitory activity.

The wild type C1 inhibitor has isoleucine and valine at positions 440 and 442, respectively. Mutations at position 440 and 442 are termed $P_5$ and $P_3$ muteins, respectively. The figures show that muteins altered only at $P_3$ (Ala, Gly, Arg, Leu or Thr substituted for Val) display different properties depending on the target protease used. When solid phase C1s is used, complex formation occurs in the order Arg=Gly<Ala<Leu<wild-type=Thr.

Further, it appears that two variants, $P_5$-leu:$P_3$-ala; and $P_5$-leu:$P_3$-leu show significantly reduced susceptibility to inactivation. The amount of HNE needed for 50% inactivation, as determined by residual functional activity towards C1s, is increased by a factor 5 to 8 compared to wild type C1 inhibitor (FIG. 5).

C1 Pegylated Muteins

The preferred embodiment C1 muteins consists of modified muteins that have a substantially longer in vivo circulating lifetime than the unmodified molecules. Favored modified C1 inhibitor muteins are those having a water soluble polymer bound to the muteins. Exemplary of such water soluble polymers are polyacrylic acid, and derivatives thereof, dextran, carboxymethylcellulose, polyethylene glycol, and polyoxyethylated glycerol. The preferred embodiment water soluble polymer is polyethylene glycol. It is disclosed in U.S. Pat. No. 4,179,337, along with methods for binding polyethylene glycol to proteins. Polyethylene glycol modified IL-2 is shown in U.S. Pat. No. 4,766,106. Using the compositions and procedures described in these two patents, polyethylene glycol modified C1 muteins are readily produced by those skilled in the art.

Administration of C1 Muteins

It will be appreciated by those skilled in the art that the C1 muteins described herein can be administered to mammals, including humans, either alone or in combination with other anti-inflammatory agents, or they may be combined with various pharmaceutically acceptable diluents or carriers. Such are widely known to those skilled in the an and are formulated according to standard pharmaceutical practices.

Exemplary diluents include physiologic saline, or buffered saline, as well as Ringer's and dextrose injection fluid, and dextrose saline and lactated Ringer's injection or diluent solutions containing additional therapeutic agents, preferably antibiotics or antibody known to be efficacious in the treatment of sepsis. Such antibody would include those known to be beneficial for the therapeutic treatment of sepsis caused by different strains of bacteria, preferably *Pseudomonas aeruginosa, Escherichia coli*, Proteus, Klebsiella, Enterobacter and Serratia.

Therapeutic Application of C1 Inhibitor Muteins

One embodiment of the invention is the administration of an effective amount of the subject C1 inhibitor muteins to individuals that are at a high risk of developing sepsis or that have developed sepsis. An example of the former category are patients about to undergo surgery. While the mode of administration is not particularly important, parenteral administration is preferred because of the rapid progression of sepsis, and thus, the need to have the C1 inhibitor muteins compositions disseminate quickly throughout the body. The preferred mode of administration is to deliver an I. V. bolus slightly before, during, or after surgery. The dosage of the C1 inhibitors will normally be determined by the prescribing physician. It is to be expected that the dosage will vary according to the age, weight and response of the individual patient.

The present invention has been described with reference to specific embodiments. However, this application is intended to cover those changes and substitutions which may be made by those skilled in the art without departing from the spirit and the scope of the appended claims.

We claim:

1. A recombinant C1 inhibitor mutein comprising an amino acid sequence in accordance with SEQ ID NO: 8, modified to wherein the amino acid at position 440 of said sequence is replaced or deleted.

2. The recombinant C1 inhibitor mutein of claim 1 wherein said amino acid at position 440 is replaced with a neutral amino acid.

3. The recombinant C1 inhibitor mutein of claim 1 wherein said amino acid at position 440 is replaced with a charged amino acid.

4. The recombinant C1 inhibitor mutein of claim 3 wherein said charged amino acid is arginine.

5. The recombinant C1 inhibitor mutein of claim 2, wherein said neutral amino acid is selected from the group consisting of alanine, glycine, leucine and threonine.

6. A recombinant C1 inhibitor mutein having an amino acid sequence in accordance with SEQ ID NO: 8 modified to wherein the amino acids at positions 440 and 442 of said sequence are replaced.

7. The recombinant C1 inhibitor mutein of claim 6, wherein said amino acid at position 442 is replaced with a neutral amino acid.

8. The recombinant C1 inhibitor mutein of claim 6, wherein said amino acid at position 442 is replaced with a charged amino acid.

9. The recombinant C1 inhibitor mutein of claim 8, wherein said charged amino acid is arginine.

10. The recombinant C1 inhibitor mutein of claim 7, wherein said neutral amino acid is selected frown the group consisting of alanine, glycine, leucine, and threonine.

11. The recombinant C1 inhibitor mutein of claim 7, wherein the amino acids at positions 440 and 442 are replaced by neutral amino acids, respectively.

12. The recombinant C1 inhibitor mutein of claim 11, wherein the amino acids at positions 440 and 442 are replaced by the neutral amino acids alanine and leucine, respectively.

13. The recombinant C1 inhibitor mutein of claim 11, wherein the amino acids at positions 440 and 442 are replaced by the neutral amino acids alanine and valine, respectively.

14. The recombinant C1 inhibitor mutein of claim 11, wherein the amino acids at positions 440 and 442 are each replaced by the neutral amino acid leucine, respectively.

15. The recombinant C1 inhibitor mutein of claim 11, wherein the amino acids at positions 440 and 442 are replaced by the neutral amino acids leucine and valine, respectively.

16. A composition for the therapeutic or prophylactic treatment of sepsis comprising a therapeutically-effective amount of a biologically-active C1 inhibitor mutein as described in claim 5.

17. A composition for the therapeutic or prophylactic treatment of sepsis comprising a therapeutically-effective amount of a biologically-active C1 inhibitor mutein as described in claim 10.

18. A composition for the therapeutic or prophylactic treatment of sepsis comprising a therapeutically-effective amount of a biologically-active C1 inhibitor mutein as described in claim 15.

19. A composition for the therapeutic or prophylactic treatment of sepsis comprising a therapeutically effective amount of a recombinant C1 inhibitor having an amino acid sequence in accordance with SEQ ID NO: 8, modified so that the amino acids at positions 440 and 442 of said sequence are the same or different and a member of the group consisting of alanine, valine, leucine and threonine.

20. The composition of claim 19 wherein the amino acids at positions 440 and 442 are alanine and valine, respectively.

21. The composition of claim 19 wherein the amino acids at positions 440 and 442 are alanine and leucine, respectively.

22. The composition of claim 19 wherein the amino acids at positions 440 and 442 are leucine and leucine, respectively.

23. A method for treating sepsis comprising administering to a patient in need of treatment a therapeutically effective amount of the composition of claim 16.

24. A method for treating sepsis comprising administering to a patient in need of treatment a therapeutically effective amount of the composition of claim 17.

25. A method for treating sepsis comprising administering to a patient in need of treatment a therapeutically effective amount of the composition of claim 18.

* * * * *

UNITED STATES PATENT AND TRADEMARK OFFICE
CERTIFICATE OF CORRECTION

PATENT NO.    : 5,622,930
DATED         : April 22, 1997
INVENTOR(S)   : Eldering et al.

It is certified that error appears in the above-identified patent and that said Letters Patent is hereby corrected as shown below:

Title page,
OTHER PUBLICATIONS, Column 2, replace "Skrive" with -- Skriven --

Column 1,
Line 56, replace "all." with -- al. --

Column 2,
Line 44, replace "covaiently" with -- covalently --

Column 3,
Line 56, replace "or" with -- of --

Column 4,
Line 5, replace "Biochemistrye" with -- Biochemistry --
Line 57, replace "J. Am," with -- J. Am. --
Line 63, replace "MgC12" with -- $MgCl_2$ --

Column 8,
Line 16, replace "etal." with -- et al. --
Line 24, replace "pNAS" with -- PNAS --

Column 9,
Line 4, replace "stericly" with -- sterically --

Column 10,
Line 49, replace "an" with -- art --

UNITED STATES PATENT AND TRADEMARK OFFICE
CERTIFICATE OF CORRECTION

PATENT NO. : 5,622,930
DATED : April 22, 1997
INVENTOR(S) : Eldering et al.

It is certified that error appears in the above-identified patent and that said Letters Patent is hereby corrected as shown below:

Claim 12,
Line 4, replace "frown" with -- from --.

Signed and Sealed this

Twenty-sixth Day of February, 2002

Attest:

JAMES E. ROGAN
Attesting Officer     Director of the United States Patent and Trademark Office

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

GCGGGCCRSA GAGRSGGCGG AG 22

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

GGTGCGGGCG GCAGAGATGG 20

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

GGTGCGGGCT CCAGAGATGG 20

( 2 ) INFORMATION FOR SEQ ID NO:4:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

GGGTGCGGGC TCTAGAGATG GCG 23

( 2 ) INFORMATION FOR SEQ ID NO:5:

( i ) SEQUENCE CHARACTERISTICS:

```
              ( A ) LENGTH: 17 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:5:

GCGGGCCAGA GAGATGG                                                                 17

( 2 ) INFORMATION FOR SEQ ID NO:6:

( i ) SEQUENCE CHARACTERISTICS:
              ( A ) LENGTH: 23 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:6:

GGGTGCGGGC GGTAGAGATG GCG                                                          23

( 2 ) INFORMATION FOR SEQ ID NO:7:

( i ) SEQUENCE CHARACTERISTICS:
              ( A ) LENGTH: 1810 base pairs
              ( B ) TYPE: nucleic acid
              ( C ) STRANDEDNESS: single
              ( D ) TOPOLOGY: linear ( i i ) MOLECULE TYPE: protein ( i x ) FEATURE:
              ( A ) NAME/KEY: CDS
              ( B ) LOCATION: 36..1535

( i x ) FEATURE:
              ( A ) NAME/KEY: mat_peptide
              ( B ) LOCATION: 102..1535

( x i ) SEQUENCE DESCRIPTION: SEQ ID NO:7:

CCAGAAGTTT GGAGTCCGCT GACGTCGCCG CCCAG ATG GCC TCC AGG CTG ACC                     53
                                       Met Ala Ser Arg Leu Thr
                                       -22         -20

CTG CTG ACC CTC CTG CTG CTG CTG GCT GGG GAT AGA GCC TCC TCA                       101
Leu Leu Thr Leu Leu Leu Leu Leu Ala Gly Asp Arg Ala Ser Ser
    -15              -10                   -5

AAT CCA AAT GCT ACC AGC TCC AGC TCC CAG GAT CCA GAG AGT TTG CAA                   149
Asn Pro Asn Ala Thr Ser Ser Ser Ser Gln Asp Pro Glu Ser Leu Gln
 1           5                       10                  15

GAC AGA GGC GAA GGG AAG GTC GCA ACA ACA GTT ATC TCC AAG ATG CTA                   197
Asp Arg Gly Glu Gly Lys Val Ala Thr Thr Val Ile Ser Lys Met Leu
         20              25                      30

TTC GTT GAA CCC ATC CTG GAG GTT TCC AGC TTG CCG ACA ACC AAC TCA                   245
Phe Val Glu Pro Ile Leu Glu Val Ser Ser Leu Pro Thr Thr Asn Ser
         35              40                      45

ACA ACC AAT TCA GCC ACC AAA ATA ACA GCT AAT ACC ACT GAT GAA CCC                   293
Thr Thr Asn Ser Ala Thr Lys Ile Thr Ala Asn Thr Thr Asp Glu Pro
     50                  55                      60

ACC ACA CAA CCC ACC ACA GAG CCC ACC ACC CAA CCC ACC ATC CAA CCC                   341
Thr Thr Gln Pro Thr Thr Glu Pro Thr Thr Gln Pro Thr Ile Gln Pro
 65              70                  75                      80

ACC CAA CCA ACT ACC CAG CTC CCA ACA GAT TCT CCT ACC CAG CCC ACT                   389
Thr Gln Pro Thr Thr Gln Leu Pro Thr Asp Ser Pro Thr Gln Pro Thr
                 85                  90                      95

ACT GGG TCC TTC TGC CCA GGA CCT GTT ACT CTC TGC TCT GAC TTG GAG                   437
```

|  |  |  |  |  |  |  |  |  |  |  |  |  |  |  |  |
|---|---|---|---|---|---|---|---|---|---|---|---|---|---|---|---|
| Thr | Gly | Ser | Phe<br>100 | Cys | Pro | Gly | Pro | Val<br>105 | Thr | Leu | Cys | Ser | Asp<br>110 | Leu | Glu |

```
AGT CAT TCA ACA GAG GCC GTG TTG GGG GAT GCT TTG GTA GAT TTC TCC        485
Ser His Ser Thr Glu Ala Val Leu Gly Asp Ala Leu Val Asp Phe Ser
    115             120                 125

CTG AAG CTC TAC CAC GCC TTC TCA GCA ATG AAG AAG GTG GAG ACC AAC        533
Leu Lys Leu Tyr His Ala Phe Ser Ala Met Lys Lys Val Glu Thr Asn
130             135                 140

ATG GCC TTT TCC CCA TTC AGC ATC GCC AGC CTC CTT ACC CAG GTC CTG        581
Met Ala Phe Ser Pro Phe Ser Ile Ala Ser Leu Leu Thr Gln Val Leu
145             150                 155                 160

CTC GGG GCT GGG CAG AAC ACC AAA ACA AAC CTG GAG AGC ATC CTC TCT        629
Leu Gly Ala Gly Gln Asn Thr Lys Thr Asn Leu Glu Ser Ile Leu Ser
                165                 170                 175

TAC CCC AAG GAC TTC ACC TGT GTC CAC CAG GCC CTG AAG GGC TTC ACG        677
Tyr Pro Lys Asp Phe Thr Cys Val His Gln Ala Leu Lys Gly Phe Thr
            180                 185                 190

ACC AAA GGT GTC ACC TCA GTC TCT CAG ATC TTC CAC AGC CCA GAC CTG        725
Thr Lys Gly Val Thr Ser Val Ser Gln Ile Phe His Ser Pro Asp Leu
        195                 200                 205

GCC ATA AGG GAC ACC TTT GTG AAT GCC TCT CGG ACC CTG TAC AGC AGC        773
Ala Ile Arg Asp Thr Phe Val Asn Ala Ser Arg Thr Leu Tyr Ser Ser
    210                 215                 220

AGC CCC AGA GTC CTA AGC AAC AAC AGT GAC GCC AAC TTG GAG CTC ATC        821
Ser Pro Arg Val Leu Ser Asn Asn Ser Asp Ala Asn Leu Glu Leu Ile
225             230                 235                 240

AAC ACC TGG GTG GCC AAG AAC ACC AAC AAG ATC AGC CGG CTG CTA            869
Asn Thr Trp Val Ala Lys Asn Thr Asn Asn Lys Ile Ser Arg Leu Leu
                245                 250                 255

GAC AGT CTG CCC TCC GAT ACC CGC CTT GTC CTC CTC AAT GCT ATC TAC        917
Asp Ser Leu Pro Ser Asp Thr Arg Leu Val Leu Leu Asn Ala Ile Tyr
            260                 265                 270

CTG AGT GCC AAG TGG AAG ACA ACA TTT GAT CCC AAG AAA ACC AGA ATG        965
Leu Ser Ala Lys Trp Lys Thr Thr Phe Asp Pro Lys Lys Thr Arg Met
        275                 280                 285

GAA CCC TTT CAC TTC AAA AAC TCA GTT ATA AAA GTG CCC ATG ATG AAT       1013
Glu Pro Phe His Phe Lys Asn Ser Val Ile Lys Val Pro Met Met Asn
    290                 295                 300

AGC AAG AAG TAC CCT GTG GCC CAT TTC ATT GAC CAA ACT TTG AAA GCC       1061
Ser Lys Lys Tyr Pro Val Ala His Phe Ile Asp Gln Thr Leu Lys Ala
305             310                 315                 320

AAG GTG GGG CAG CTG CAG CTC TCC CAC AAT CTG AGT TTG GTG ATC CTG       1109
Lys Val Gly Gln Leu Gln Leu Ser His Asn Leu Ser Leu Val Ile Leu
                325                 330                 335

GTA CCC CAG AAC CTG AAA CAT CGT CTT GAA GAC ATG GAA CAG GCT CTC       1157
Val Pro Gln Asn Leu Lys His Arg Leu Glu Asp Met Glu Gln Ala Leu
            340                 345                 350

AGC CCT TCT GTT TTC AAG GCC ATC ATG GAG AAA CTG GAG ATG TCC AAG       1205
Ser Pro Ser Val Phe Lys Ala Ile Met Glu Lys Leu Glu Met Ser Lys
        355                 360                 365

TTC CAG CCC ACT CTC CTA ACA CTA CCC CGC ATC AAA GTG ACG ACC AGC       1253
Phe Gln Pro Thr Leu Leu Thr Leu Pro Arg Ile Lys Val Thr Thr Ser
    370                 375                 380

CAG GAT ATG CTC TCA ATC ATG GAG AAA TTG GAA TTC TTC GAT TTT TCT       1301
Gln Asp Met Leu Ser Ile Met Glu Lys Leu Glu Phe Phe Asp Phe Ser
385             390                 395                 400

TAT GAC CTT AAC CTG TGT GGG CTG ACA GAG GAC CCA GAT CTT CAG GTT       1349
Tyr Asp Leu Asn Leu Cys Gly Leu Thr Glu Asp Pro Asp Leu Gln Val
            405                 410                 415

TCT GCG ATG CAG CAC CAG ACA GTG CTG GAA CTG ACA GAG ACT GGG GTG       1397
```

| Ser | Ala | Met | Gln | His | Gln | Thr | Val | Leu | Glu | Leu | Thr | Glu | Thr | Gly | Val | |
|---|---|---|---|---|---|---|---|---|---|---|---|---|---|---|---|---|
| | | 420 | | | | | 425 | | | | | | 430 | | | |

| GAG | GCG | GCT | GCA | GCC | TCC | GCC | ATC | TCT | GTG | GCC | CGC | ACC | CTG | CTG | GTC | 1445 |
|---|---|---|---|---|---|---|---|---|---|---|---|---|---|---|---|---|
| Glu | Ala | Ala | Ala | Ala | Ser | Ala | Ile | Ser | Val | Ala | Arg | Thr | Leu | Leu | Val | |
| | | 435 | | | | 440 | | | | | 445 | | | | | |

| TTT | GAA | GTG | CAG | CAG | CCC | TTC | CTC | TTC | GTG | CTC | TGG | GAC | CAG | CAG | CAC | 1493 |
|---|---|---|---|---|---|---|---|---|---|---|---|---|---|---|---|---|
| Phe | Glu | Val | Gln | Gln | Pro | Phe | Leu | Phe | Val | Leu | Trp | Asp | Gln | Gln | His | |
| | | 450 | | | | 455 | | | | | 460 | | | | | |

| AAG | TTC | CCT | GTC | TTC | ATG | GGG | CGA | GTA | TAT | GAC | CCC | AGG | GCC | | | 1535 |
|---|---|---|---|---|---|---|---|---|---|---|---|---|---|---|---|---|
| Lys | Phe | Pro | Val | Phe | Met | Gly | Arg | Val | Tyr | Asp | Pro | Arg | Ala | | | |
| 465 | | | | | 470 | | | | | 475 | | | | | | |

| TGAGACCTGC | AGGATCAGGT | TAGGGCGAGC | GCTACCTCTC | CAGCCTCAGC | TCTCAGTTGC | 1595 |
|---|---|---|---|---|---|---|
| AGCCCTGCTG | CTGCCTGCCT | GGACTTGCCC | CTGCCACCTC | CTGCCTCAGG | TGTCCGCTAT | 1655 |
| CCACCAAAAG | GGCTCCTGAG | GGTCTGGGCA | AGGGACCTGC | TTCTATTAGC | CCTTCTCCAT | 1715 |
| GGCCCTGCCA | TGCTCTCCAA | ACCACTTTTT | GCAGCTTTCT | CTAGTTCAAG | TTCACCAGAC | 1775 |
| TCTATAAATA | AAACCTGACA | GACCATAAAA | AAAAA | | | 1810 |

(2) INFORMATION FOR SEQ ID NO:8:

(i) SEQUENCE CHARACTERISTICS:
    (A) LENGTH: 500 amino acids
    (B) TYPE: amino acid
    (D) TOPOLOGY: linear (ii) MOLECULE TYPE: protein (xi) SEQUENCE DESCRIPTION: SEQ ID NO:8:

| Met | Ala | Ser | Arg | Leu | Thr | Leu | Leu | Thr | Leu | Leu | Leu | Leu | Leu | Leu | Ala |
|---|---|---|---|---|---|---|---|---|---|---|---|---|---|---|---|
| -22 | | -20 | | | | | -15 | | | | | -10 | | | |

| Gly | Asp | Arg | Ala | Ser | Ser | Asn | Pro | Asn | Ala | Thr | Ser | Ser | Ser | Ser | Gln |
|---|---|---|---|---|---|---|---|---|---|---|---|---|---|---|---|
| | -5 | | | | | 1 | | | | 5 | | | | | 10 |

| Asp | Pro | Glu | Ser | Leu | Gln | Asp | Arg | Gly | Glu | Gly | Lys | Val | Ala | Thr | Thr |
|---|---|---|---|---|---|---|---|---|---|---|---|---|---|---|---|
| | | | | 15 | | | | | 20 | | | | | 25 | |

| Val | Ile | Ser | Lys | Met | Leu | Phe | Val | Glu | Pro | Ile | Leu | Glu | Val | Ser | Ser |
|---|---|---|---|---|---|---|---|---|---|---|---|---|---|---|---|
| | | | 30 | | | | | 35 | | | | | 40 | | |

| Leu | Pro | Thr | Thr | Asn | Ser | Thr | Thr | Asn | Ser | Ala | Thr | Lys | Ile | Thr | Ala |
|---|---|---|---|---|---|---|---|---|---|---|---|---|---|---|---|
| | | | 45 | | | | 50 | | | | | 55 | | | |

| Asn | Thr | Thr | Asp | Glu | Pro | Thr | Thr | Gln | Pro | Thr | Thr | Glu | Pro | Thr | Thr |
|---|---|---|---|---|---|---|---|---|---|---|---|---|---|---|---|
| | 60 | | | | | 65 | | | | | 70 | | | | |

| Gln | Pro | Thr | Ile | Gln | Pro | Thr | Gln | Pro | Thr | Thr | Gln | Leu | Pro | Thr | Asp |
|---|---|---|---|---|---|---|---|---|---|---|---|---|---|---|---|
| 75 | | | | | 80 | | | | | 85 | | | | | 90 |

| Ser | Pro | Thr | Gln | Pro | Thr | Thr | Gly | Ser | Phe | Cys | Pro | Gly | Pro | Val | Thr |
|---|---|---|---|---|---|---|---|---|---|---|---|---|---|---|---|
| | | | | 95 | | | | | 100 | | | | | 105 | |

| Leu | Cys | Ser | Asp | Leu | Glu | Ser | His | Ser | Thr | Glu | Ala | Val | Leu | Gly | Asp |
|---|---|---|---|---|---|---|---|---|---|---|---|---|---|---|---|
| | | | 110 | | | | | 115 | | | | | 120 | | |

| Ala | Leu | Val | Asp | Phe | Ser | Leu | Lys | Leu | Tyr | His | Ala | Phe | Ser | Ala | Met |
|---|---|---|---|---|---|---|---|---|---|---|---|---|---|---|---|
| | | 125 | | | | | 130 | | | | | 135 | | | |

| Lys | Lys | Val | Glu | Thr | Asn | Met | Ala | Phe | Ser | Pro | Phe | Ser | Ile | Ala | Ser |
|---|---|---|---|---|---|---|---|---|---|---|---|---|---|---|---|
| | 140 | | | | | 145 | | | | | 150 | | | | |

| Leu | Leu | Thr | Gln | Val | Leu | Leu | Gly | Ala | Gly | Gln | Asn | Thr | Lys | Thr | Asn |
|---|---|---|---|---|---|---|---|---|---|---|---|---|---|---|---|
| 155 | | | | | 160 | | | | | 165 | | | | | 170 |

| Leu | Glu | Ser | Ile | Leu | Ser | Tyr | Pro | Lys | Asp | Phe | Thr | Cys | Val | His | Gln |
|---|---|---|---|---|---|---|---|---|---|---|---|---|---|---|---|
| | | | | 175 | | | | | 180 | | | | | 185 | |

| Ala | Leu | Lys | Gly | Phe | Thr | Thr | Lys | Gly | Val | Thr | Ser | Val | Ser | Gln | Ile |
|---|---|---|---|---|---|---|---|---|---|---|---|---|---|---|---|
| | | | 190 | | | | | 195 | | | | | 200 | | |

| Phe | His | Ser | Pro | Asp | Leu | Ala | Ile | Arg | Asp | Thr | Phe | Val | Asn | Ala | Ser |
|---|---|---|---|---|---|---|---|---|---|---|---|---|---|---|---|

|  | 205 |  |  |  |  | 210 |  |  |  |  | 215 |  |  |  |
|---|---|---|---|---|---|---|---|---|---|---|---|---|---|---|
| Arg | Thr 220 | Leu | Tyr | Ser | Ser | Ser 225 | Pro | Arg | Val | Leu | Ser 230 | Asn | Asn | Ser | Asp |
| Ala 235 | Asn | Leu | Glu | Leu | Ile 240 | Asn | Thr | Trp | Val | Ala 245 | Lys | Asn | Thr | Asn | Asn 250 |
| Lys | Ile | Ser | Arg | Leu 255 | Leu | Asp | Ser | Leu | Pro 260 | Ser | Asp | Thr | Arg | Leu 265 | Val |
| Leu | Leu | Asn | Ala 270 | Ile | Tyr | Leu | Ser | Ala 275 | Lys | Trp | Lys | Thr | Thr 280 | Phe | Asp |
| Pro | Lys | Lys 285 | Thr | Arg | Met | Glu | Pro 290 | Phe | His | Phe | Lys | Asn 295 | Ser | Val | Ile |
| Lys | Val 300 | Pro | Met | Met | Asn | Ser 305 | Lys | Lys | Tyr | Pro | Val 310 | Ala | His | Phe | Ile |
| Asp 315 | Gln | Thr | Leu | Lys | Ala 320 | Lys | Val | Gly | Gln | Leu 325 | Gln | Leu | Ser | His | Asn 330 |
| Leu | Ser | Leu | Val | Ile 335 | Leu | Val | Pro | Gln | Asn 340 | Leu | Lys | His | Arg | Leu 345 | Glu |
| Asp | Met | Glu | Gln 350 | Ala | Leu | Ser | Pro | Ser 355 | Val | Phe | Lys | Ala | Ile 360 | Met | Glu |
| Lys | Leu | Glu 365 | Met | Ser | Lys | Phe | Gln 370 | Pro | Thr | Leu | Leu | Thr 375 | Leu | Pro | Arg |
| Ile | Lys 380 | Val | Thr | Thr | Ser | Gln 385 | Asp | Met | Leu | Ser | Ile 390 | Met | Glu | Lys | Leu |
| Glu 395 | Phe | Phe | Asp | Phe | Ser 400 | Tyr | Asp | Leu | Asn | Leu 405 | Cys | Gly | Leu | Thr | Glu 410 |
| Asp | Pro | Asp | Leu | Gln 415 | Val | Ser | Ala | Met | Gln 420 | His | Gln | Thr | Val | Leu 425 | Glu |
| Leu | Thr | Glu | Thr 430 | Gly | Val | Glu | Ala | Ala 435 | Ala | Ala | Ser | Ala | Ile 440 | Ser | Val |
| Ala | Arg | Thr 445 | Leu | Leu | Val | Phe | Glu 450 | Val | Gln | Gln | Pro | Phe 455 | Leu | Phe | Val |
| Leu | Trp 460 | Asp | Gln | Gln | His | Lys 465 | Phe | Pro | Val | Phe | Met 470 | Gly | Arg | Val | Tyr |
| Asp 475 | Pro | Arg | Ala |  |  |  |  |  |  |  |  |  |  |  |  |